United States Patent [19]

Gaffar et al.

[11] Patent Number: 5,648,064

[45] Date of Patent: Jul. 15, 1997

[54] ORAL COMPOSITIONS HAVING ACCELERATED TOOTH WHITENING EFFECT

[76] Inventors: Abdul Gaffar, 89 Carter Rd., Princeton, N.J. 08902; Sahar Fakhry-Smith, 7 Ryans Ct., Bordentown, N.J. 08505

[21] Appl. No.: 499,532

[22] Filed: Jul. 7, 1995

[51] Int. Cl.[6] .................... A61K 7/16; A61K 7/20
[52] U.S. Cl. .................... 424/53; 424/49
[58] Field of Search .................... 424/53, 49–58

[56] References Cited

U.S. PATENT DOCUMENTS

| | | | |
|---|---|---|---|
| 4,728,455 | 3/1988 | Rerek | 252/99 |
| 4,759,956 | 7/1988 | Amer et al. | 427/213 |
| 5,032,178 | 7/1991 | Cornell | 106/35 |
| 5,194,416 | 3/1993 | Jureller et al. | 502/167 |
| 5,256,402 | 10/1993 | Prencipe et al. | 424/53 |
| 5,279,816 | 1/1994 | Church et al. | 424/53 |
| 5,302,374 | 4/1994 | Wagner | 424/52 |
| 5,302,375 | 4/1994 | Viscio | 424/53 |
| 5,356,554 | 10/1994 | Delwel et al. | 252/94 |
| 5,536,441 | 7/1996 | Chapple et al. | 252/186.33 |

FOREIGN PATENT DOCUMENTS 0237111  9/1987  European Pat. Off. .......... C11D 3/39

*Primary Examiner*—Shep K. Rose
*Attorney, Agent, or Firm*—Paul Shapiro

[57]  ABSTRACT

A two component whitening dentifrice composition is disclosed which comprises a first component containing a peroxygen compound such as hydrogen peroxide and a second dentifrice component containing a manganese coordination complex compound such as manganese gluconate, which activates the peroxygen compound and accelerates the release of active oxygen for rapid whitening action, the first and second components being maintained separate from the other until dispensed for application to teeth.

14 Claims, No Drawings

ORAL COMPOSITIONS HAVING ACCELERATED TOOTH WHITENING EFFECT

BACKGROUND OF THE INVENTION

1. Field of the Invention

This invention relates generally to an oral composition which when applied onto the surface of teeth acts to whiten teeth and more particularly to an oral composition for whitening teeth that is more effective than existing products available to the consumer.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth.

There are available in the marketplace oral compositions for home use which contain 1–3% by weight concentrations of a peroxygen compound such as hydrogen peroxide and when applied on the teeth effect whitening of stains. However, these compositions are considered to have a slow bleaching effect.

Illustrative of oral compositions containing peroxygen compounds for whitening teeth include U.S. Pat. Nos. 5,302,374, 5,279,816, 4,988,450; 4,980,152, 4,839,156, 4,405,599, 3,988433 and 3,657,417.

U.S. Pat. No. 5,279,816 discloses an oral composition for whitening teeth containing peracetic acid dissolved or suspended in a vehicle. U.S. Pat. No. 5,302,374 discloses generating peracetic acid within a dentifrice vehicle by combining water, acetylsalicylic acid and a water soluble alkali metal percarbonate.

U.S. Pat. Nos. 4,988,450 and 3,657,417 disclose formulating oxygen liberating compositions for the whitening of teeth utilizing anhydrous pastes or gels.

U.S. Pat. No. 4,980,152 discloses an aqueous oral gel composition comprising about 0.5 to about 10% by weight urea peroxide and 0.01 to 2% by weight of a fluoride providing compound.

U.S. Pat. No. 4,839,156 discloses a water containing a hydrogen peroxide-Pluronic thickened oral gel composition.

U.S. Pat. No. 4,405,599 discloses a toothpaste containing a combination of calcium peroxide and sodium perborate oxidizing agents, dicalcium phosphate, calcium carbonate and magnesium carbonate cleaning agents, sorbitol humectant, cornstarch and cellulose gum thickening agents, and an anionic detergent.

U.S. Pat. No. 3,988,433 discloses oral compositions containing peroxyacids and alkyl diperoxy acids having alkylene groups containing 5–11 carbon atoms which remove stain from teeth.

In those applications where oral compositions are designed for home use whitening of teeth, it is essential that the peroxide generating components react quickly since the user will normally wish to limit the time in which the whitening composition is in contact with the teeth. To accomplish this, applicant has recognized the desirability of accelerating the breakdown of peroxygen compounds and the release of active oxygen within the oral cavity to effect a more rapid whitening of the teeth.

SUMMARY OF THE INVENTION

In accordance with the present invention there is provided a peroxygen oral composition for accelerated whitening of teeth wherein there is provided a two component composition of separate unmixed phases comprised of (a) a first component containing a water soluble peroxygen compound contained in an orally acceptable vehicle and unmixed (b) a second component containing a manganese coordination complex compound in an orally acceptable vehicle in an amount effective to activate the peroxygen compound and accelerate the release of active oxygen, the two phases being combined shortly before application to the teeth wherein the manganese compound interacts with the peroxygen constituent to accelerate the breakdown and rapid release of active oxygen from the peroxygen compound such rapid release being effective for whitening teeth when allowed to remain on the teeth for a limited time.

The present invention offers the advantages that active oxygen is generated quickly and in large quantities thereby facilitating convenient and effective home use by the consumer as well as professional use by the dentist.

DETAILED DESCRIPTION OF THE INVENTION

Peroxygen compounds useful in the oral compositions of the invention include hydrogen peroxide, peroxydiphosphate, urea peroxide, metal peroxides such as calcium peroxide, sodium peroxide, stronthium peroxide, magnesium peroxide, and the salts of perborate, persilicate, perphosphate and percarbonate such as sodium perborate, potassium persilicate and sodium percarbonate. The most suitable peroxygen compound for this invention is hydrogen peroxide.

Manganese coordination complexes suitable for use as activator compounds in the practice of the present invention include a complex of manganese (III) and a multidentate ligand supplied by a complexing agent, such activator compounds being known to the art and more fully described in U.S. Pat. No. 4,728,455, the disclosure of which is incorporated herein by reference. Activators preferred for use to accelerate the breakdown of peroxygen compounds and the release of active oxygen in accordance with the practice of the present invention include a complex of manganese (III) and a multidentate ligand supplied by a hydroxy carboxylic acid complexing agent containing at least 5 carbon atoms including hexonic hydroxy acids such as gluconic acid, gulonic acid, idonic acids such as glucouronic acid, galactouronic acid and mannuronic acid, heptonic hydroxy acids such as glucoheptanoic acid and sugars such as saccharic acid and isosaccharic acid. A most preferred compound is Mn (III) gluconate.

Other useful manganese coordination complex compounds suitable for use in the practice of the present invention include manganese complexes of the formula L_n Mm X wherein Mn is manganese in the +3 or +4 oxidation state; n and m are integers from 1 to 4; X represents a coordination or a bridging species that coordinates with the manganese and is selected from $H_2O$, $OH^-$, $O_2^-$, $SH^-$, and alkyl and aryl groups having 1 to 20 carbon atoms and L is a ligand having at least 2 nitrogen, phosphorus, oxygen or sulfur atoms coordinating with the manganese.

Examples of ligands suitable for the formation of the manganese complexes of the formula are more fully described in U.S. Pat. No. 5,194,416, such description being incorporated herein by reference. Preferred examples of L in the formula above include: 1,4,7-triazacyclononane, 1,4,7-triazacyclodecane, 1,4,8-triazacycloundecane, 1,5,9-triazacyclodecane, 1,4,7-trimethyl-1,4,7-triazacyclononane, 1,4,7-trimethyl-1,4,7-triazacyclodecane, 1,4,8-trimethyl-1,4,8-triazacycloundecane, 1,5,9-trimethyl-1,5,9-triazacyclododecane, tris(pyridin-2-yl) methane, tris(pyrazol-1-yl)methane, tris(imidazol-2-yl)methane, tris(pyridin-2-yl) borate, tris(imidazol-2-yl)phosphine, 1,1,1-tris(methylamino)ethane, Bis(pyridin-2-yl-methyl)amine, Bis(triazol-1-yl-methyl)amine and Bis(imidazol-2-yl-methyl)amine The amount of peroxygen compound incorporated in the first component of the two component oral composition of the present invention will vary dependent upon its intended use. For use by trained professionals in office treatments, the concentration of peroxygen compound incorporated in the oral composition can vary from about 5 to about 30% by weight. For home use, such high concentrations of peroxygen compounds cannot be used safely by the typical consumer and therefore the useful range of peroxygen compound when the oral composition is a paste, gel or rinse is between 0.1 to 3.0% by weight. The preferred range is between about 0.5 to about 2.0% by weight.

The amount of manganese complex activator compound present in the second component of the two phase whitening oral composition of the present invention will vary dependent upon the amount of peroxygen compound incorporated in the first component. When the whitening oral composition is to be used by trained professionals and the first component contains relatively high concentrations of a peroxygen compound, e.g. 5 to 35% by weight, the amount of manganese activator compound incorporated in the second component will range between 0.1 to 3% by weight and preferably between 0.25 to 1.75% by weight. For home use oral compositions in which the concentration range of peroxygen compound in the first oral composition component is between about 0.1 to about 3.0% by weight, lower concentrations, e.g., between about 0.001 to about 0.3% by weight of the manganese activator is included in the second component and preferably about 0.0025 to about 0.15% by weight of the activator is used.

The vehicle used to prepare the individual components of the oral composition of the present invention is substantially the same for both components and includes water and a suitable humectant such as glycerin, propylene glycol, polyethylene glycol, or any suitable mixture thereof. A mixture of glycerin and polyethylene glycol is preferred as the humectant in the practice of the present invention.

The proportion of vehicle in each of the the dentifrice components of the present invention is generally within the range of about 40 to about 80% by weight of the paste or gel dentifrice component of this invention and preferably about 50 to about 65% by weight of the dentifrice component.

A surfactant is used in the preparation of oral composition components of the present invention to aid in the thorough dispersion of the composition throughout the oral cavity when applied thereto as well as to improve the cosmetic acceptability and detersive and foaming properties of the composition. Among surfactants useful in the practice of the present invention are salts of the higher alkyl sulfates and alkyl phosphates having 8 to 18 carbon atoms in the alkyl group such as sodium lauryl sulfate and sodium lauryl phosphate, sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acids, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids.

The surfactant is included in the vehicles of the oral composition components of the present invention at a concentration of about 0.5 to about 3.0% by weight and preferably about 1.0 to about 2.0% by weight.

To prepare dentifrice components, polishing agents are incorporated in both components of the present invention and preferred polishing agents are siliceous materials, such as silica, which have a mean particle size up to about 20 microns. A preferred silica is a precipitated amorphous hydrated silica, such as Sorbosil AC-35 marketed by Crosfield Chemicals, or Zeodent 115 from J.M. Huber Company but other polishing agents may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

The polishing agent is present in the dentifrice compositions of the present invention at a concentration of about 10 to about 30% by weight and preferably 15 to about 25% by weight.

Inorganic thickeners may be included in the dentifrices of the present invention and include fumed silicas such as Cabosil available from Cabot Corporation, and thickening silicas including those available from W. R. Grace designated Sylox 15.

Organic thickeners such as natural and synthetic gums and colloids may also be incorporated in the dentifrice compositions of the present invention. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose and hydroxyethyl cellulose.

The inorganic or organic thickener may be incorporated in dentifrice components of the present invention at a concentration of about 0.05 to about 2% by weight and preferably about 0.1 to about 1.5% by weight.

Fluoride-providing salts having anti-caries efficacy may also be incorporated in the oral compositions of the present invention and are characterized by their ability to release fluoride ions in water. It is preferable to employ a water-soluble salt fluoride providing about 10–5,000 ppm of fluoride ion and preferably about 1000–1500 ppm of fluoride ion. Among these materials are water-soluble alkali metal salts, for example, sodium fluoride, potassium fluoride, sodium monofluorophosphate and sodium fluorosilicate.

Sodium fluoride and sodium monofluorophosphate are preferred fluoride-providing salts.

Salts having anti-tartar efficacy, including water soluble salts, such as dialkali or tetra-alkali metal pyrophosphate salts such as $Na_4P_2O_7$(TSPP) $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may be incorporated in the dentifrice compositions of the present invention preferably at a concentration of about 0.5 to about 8.0% by weight.

A striped dentifrice product is obtained in accordance with the practice of the present invention wherein colorants of contrasting colors are incorporated in each of the dentifrice components used in the practice of the present invention, the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentifrice component and are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1 -p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydride), FD&C Blue No. 2 (sodium salt of disulfonic acid of indigotin) and mixtures thereof in various proportions. The concentration of the dye for the most effective result in the present invention is present in the dentifrice composition in an amount from about 0.0005 percent to about 2 percent by weight.

It is preferred that the colorant included in one of the dentifrice components be a pigment such as $TiO_2$ and that the colorant distributed throughout the vehicle of the other dentifrice component be a dye and that the dye be of a different color than the pigment included in the first dentifrice component. To avoid bleaching of the dye by the peroxygen compound constituent it is critical that the peroxygen compound not be included in the dentifrice component in which a peroxygen sensitive dye ingredient is included.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the oral composition components of this invention. Non-limiting examples thereof include preservatives, silicones and chlorophyll compounds, vitamins such as vitamins B6, B12, C, E and K, antibacterial agents such as chlorohexidene, halogenated diphenyl ethers such as triclosan, desensitizing agents such as potassium nitrate and potassium citrate and mixtures thereof. These adjuvants are incorporated in the oral composition components in amounts which do not substantially adversely affect the properties and characteristics desired, and are selected and used in proper amounts, depending upon the particular type of component involved.

To prepare a peroxygen compound containing dentifrice paste or gel component of the present invention, the humectants e.g. propylene glycol, glycerin, polyethylene glycol ingredients, sweetener and water are dispersed in a conventional mixer until the mixture becomes a homogeneous gel phase. Into the gel phase are added a pigment such as $TiO_2$ and any tartar control agents such as tetrasodium pyrophosphate or sodium tripolyphosphate or both and fluoride anti-caries agents such as sodium monofluorophosphate. These ingredients are mixed until a homogeneous phase is obtained. Thereafter the thickener, polishing agent, peroxygen compound, flavor and surfactant ingredients are added and the ingredients mixed at high speed under vacuum of about 20–100 mm Hg. The resultant product is a homogeneous, semi-solid, extrudable paste product.

To prepare the second dye containing component, the procedure identical to that described above is employed except that dye ingredients and activator compounds are incorporated in the initial mixture of humectants and sweetener and $TiO_2$ and the peroxygen compound is omitted from the dentifrice component formulation.

To prepare a rinse composition the various ingredients are mixed together in water in a conventional manner.

In packaging the oral composition of the present invention for sale, any convenient means for effecting the separation of the peroxygen compound from the activator components before use can be utilized. For example in the packaging of dentifrice components, a single container can be compartmentalized so that the peroxygen containing dentifrice component and the activator containing component are housed in separate compartments and are dispensed simultaneously for common application to a toothbrush and not admixed until applied to the teeth. Alternatively, the peroxygen containing component and the activator containing component can be housed in separate containers from which the respective phases are dispensed for admixture just prior to use.

The following examples are further illustrative of the present invention, but it is understood that the invention is not limited thereto. All amounts and proportions referred to herein and the appended claims are by weight.

EXAMPLE 1

TABLE 1

| Dual Component Dentifrice Composition | | |
|---|---|---|
| Ingredients | Component 1 Wt. % | Component 2 Wt. % |
| Deionized Water | 10.00 | 10.00 |
| Glycerin | 29.00 | 29.00 |
| Propylene Glycol | 3.00 | 3.00 |
| Polyethylene glycol 600 | 17.64 | 17.64 |

TABLE 1-continued

Dual Component Dentifrice Composition

| Ingredients | Component 1 Wt. % | Component 2 Wt. % |
| --- | --- | --- |
| Na Saccharin | 0.50 | 0.50 |
| Xanthan | 0.20 | 0.20 |
| Carboxymethyl Cellulose | 0.20 | 0.20 |
| Sodium Monofluorophosphate (MFP) | 0.76 | 0.76 |
| Tetrasodium Pyrophosphate (TSPP) | 2.00 | 2.00 |
| Sodium Tripolyphosphate (STPP) | 3.00 | 3.00 |
| $TiO_2$ | 1.00 | 0.00 |
| FD&C - (1% Soln) (Green Color) | 0.00 | 1.00 |
| Zeodent 115 (Hydrated Silica) | 25.00 | 26.45 |
| Sylodent 15 (Amorphous Silica) | 2.00 | 2.00 |
| Sodium Lauryl Sulfate | 1.7000 | 1.70 |
| Hydrogen Peroxide | 1.00 | 0.00 |
| Manganese Gluconate | 0.00 | 0.05 |
| $Na_2CO_3$ | 2.00 | 2.00 |
| Flavor (Mint) | 1.00 | 1.00 |
| Total | 100.00 | 100.00 |

To prepare Component 1, the water, glycerin, propylene glycol, polyethylene glycol 600 and sodium saccharin ingredients were dispersed in a conventional mixer until the mixture became a slurry, which was smooth in appearance, producing a homogeneous gel phase in which the MFP, TSPP, STPP and $TiO_2$ were added by mixing to prepare a dispersion. The dispersion was transferred to a vacuum mixer, and the silceous agents, sodium carbonate, hydrogen peroxide and flavor were then added and mixed for 10 to 30 minutes at high speed under a vacuum of about 50 mm Hg, to obtain a homogeneous mixture. The resultant product was a paste with satisfactory flavor and was white in color.

Component 2 was prepared in the same manner as that used for Component 1 except the FD&C dye was substituted for the $TiO_2$ pigment and manganese gluconate substituted for hydrogen peroxide. The resultant product was a gel with satisfactory flavor and was green in color.

To test the whitening efficacy of dentifrice components 1 and 2, naturally stained human teeth were stained with a staining broth consisting of coffee, tea, mucin, microbiological media and a chromogenic microorganism. Stained teeth selected for the test showed the same amount of discoloration. To test the whitening efficacy of the gel, the teeth were immersed in 2 grams of a mixture of equal amounts of Components 1 and 2 at 37° C. Before immersion, the color of the teeth was measured with a Minolta Chromameter in which L* is a measure of response to the eye to lightness and darkness, and b* is a measure of yellowness a* is a measure of blueness. The higher the L* value and lower b* value, the whiter teeth appear.

The whitening index was calculated using the following equation:

$$\Delta E=[(\Delta L^*)^2+(\Delta a^*)^2+(\Delta b^*)^2]^{1/2}$$

The higher the ΔE the greater the whitening effect observed.

The teeth remained immersed in the mixed components for 15 minutes. The whitening index (ΔE) of the immersed teeth is summarized in Table II below.

For purposes of comparison, the procedure of Example 1 was repeated with exception that Component 2 did not contain manganese gluconate. This comparative composition was designated Composition "$C_1$". The whitening index of comparative Composition $C_1$ is also summarized in Table II below.

EXAMPLES 2 TO 5

The procedure of Example I was repeated except in separate dentifrice components urea peroxide (Example 2), sodium percarbonate (Example 3), calcium peroxide (Example 4) and peroxydiphosphate (Example 5) were substituted for hydrogen peroxide in Component 1. The dual component compositions of Examples 2–5 were also tested for whitening efficacy following the test procedure of Example I.

For purposes of comparison the procedure used to prepare the compositions of Examples 2–5 were repeated with the exception that the activator ingredient manganese gluconate was not included in Component 2. The color measurements of these comparative compositions designated $C_2$ to $C_5$, are also included in Table II below.

TABLE II

Dentifrice Composition

| Test No. | Component 1 Peroxygen Compound | Component 2 Manganese Complex | Initial | | | After 15 mins | | | |
| --- | --- | --- | --- | --- | --- | --- | --- | --- | --- |
| | | | ΔL* | Δa* | Δb* | ΔL* | Δa* | Δb* | ΔE |
| Ex. 1 | $H_2O_2$ | Mn Gluconate | 60.7 | −2.06 | 9.00 | 68.62 | −1.76 | 2.48 | 10.27 |
| $C_1$ | $H_2O_2$ | — | 61.59 | −1.58 | 7.48 | 65.25 | −1.50 | 5.99 | 5.60 |
| Ex. 2 | Urea Peroxide | Mn Gluconate | 62.15 | −1.53 | 5.05 | 68.56 | −1.56 | 7.21 | 5.68 |
| $C_2$ | Urea Peroxide | — | 64.24 | −2.24 | 8.26 | 66.99 | −2.27 | 5.60 | 3.20 |
| Ex. 3 | Na Percarbonate | Mn Gluconate | 60.43 | −1.32 | 7.96 | 69.11 | −1.49 | 4.45 | 9.46 |
| $C_3$ | Na Percarbonate | — | 65.61 | −2.02 | 8.30 | 66.62 | −2.01 | 7.96 | 2.06 |
| Ex. 4 | $CaO_2$ | Mn Gluconate | 60.96 | −1.88 | 6.97 | 71.47 | −1.61 | 2.46 | 11.70 |
| $C_4$ | $CaO_2$ | — | 60.92 | −1.68 | 8.53 | 62.16 | −1.68 | 8.99 | 1.44 |
| Ex. 5 | Peroxydiphosphate | Mn Gluconate | 59.51 | −1.88 | 7.21 | 70.84 | −1.73 | 4.13 | 11.75 |
| $C_5$ | Peroxydiphosphate | — | −62.17 | −2.18 | 7.03 | 62.94 | −2.33 | 7.06 | 1.33 |

The ΔE values recorded in Table II indicate that the activator manganese gluconate substantially increases the tooth whitening efficacy of the peroxygen compounds, hydrogen peroxide, urea peroxide, sodium percarbonate, calcium peroxide and peroxydiphosphate in the order of about 1.5 to 8 times.

What is claimed is:

1. A method of whitening stained or discolored teeth in the oral cavity which comprises applying to the teeth a two component whitening composition, which will whiten stained or discolored teeth, when applied thereto, the composition being comprised of a first component containing in a vehicle a safe amount of a peroxygen compound effective to whiten teeth, and a second component containing a manganese coordination complex compound in a vehicle, the manganese compound being present in the vehicle in an amount effective to activate the peroxygen compound, the first and second components being maintained separate from each other until dispensed for application to the teeth, dispensing and mixing the separately maintained components so that the manganese compound of the second component interacts with the peroxygen compound of the first component whereby the breakdown of the peroxygen compound and the release of active oxygen is accelerated and then allowing the mixed components to remain on the teeth for a time sufficient to effect rapid whitening thereof.

2. The method of claim 1 wherein the peroxygen compound is hydrogen peroxide.

3. The method of claim 1 wherein the peroxygen compound is urea peroxide.

4. The method of claim 1 wherein the peroxygen compound is sodium percarbonate.

5. The method of claim 1 wherein the peroxygen compound is calcium peroxide.

6. The method of claim 1 wherein the peroxygen compound is peroxydiphosphate.

7. The method of claim 1 wherein the manganese coordination complex compound is manganese gluconate.

8. A two component whitening dentifrice composition which exhibits rapid whitening of stained or discolored teeth, which composition comprises a first dentifrice component containing a peroxygen compound and a second dentifrice component containing a manganese coordination complex compound, the first and second dentifrice components being maintained separate from each other until dispensed for application to teeth requiring the removal of stain and discoloration.

9. The composition of claim 8 wherein the peroxygen compound is hydrogen peroxide.

10. The composition of claim 8 wherein the peroxygen compound is urea peroxide.

11. The composition of claim 8 wherein the peroxygen compound is sodium percarbonate.

12. The composition of claim 8 wherein the peroxygen compound is calcium peroxide.

13. The composition of claim 8 wherein the peroxygen compound is peroxydiphosphate.

14. The composition of claim 8 wherein the manganese coordination complex is manganese gluconate.

* * * * *